United States Patent [19]
Jain et al.

[11] Patent Number: 4,972,711
[45] Date of Patent: Nov. 27, 1990

[54] ISOMETRIC LIFTING DEVICE

[75] Inventors: Sanjeev Jain, Columbia; John E. Vermette, Baltimore, both of Md.

[73] Assignee: Baltimore Therapeutic Equipment Co., Hanover, Md.

[21] Appl. No.: 160,758

[22] Filed: Feb. 26, 1988

[51] Int. Cl.⁵ ............................................. A61B 5/22
[52] U.S. Cl. .............................. 73/379; 272/129.000
[58] Field of Search ............... 73/379, 862.08, 862.12, 73/380, 381; 272/125, 129

[56] References Cited

U.S. PATENT DOCUMENTS

| | | | |
|---|---|---|---|
| 373,942 | 11/1887 | Page | 73/379 |
| 3,397,884 | 8/1968 | Blasi . | |
| 3,550,449 | 12/1970 | Henson . | |
| 3,589,193 | 6/1971 | Thornton | 73/379 |
| 3,851,874 | 12/1974 | Wilkin . | |
| 3,929,331 | 12/1975 | Beeding | 73/379 X |
| 4,082,267 | 4/1978 | Flavell . | |
| 4,235,439 | 11/1980 | DeDonno | 73/379 X |
| 4,355,633 | 10/1982 | Heilbrun . | |
| 4,412,455 | 11/1983 | Borgersen | 73/862.12 |
| 4,475,408 | 10/1984 | Browning | 73/862.12 |
| 4,565,368 | 1/1986 | Boettcher . | |
| 4,592,545 | 6/1986 | Sagedahl et al. . | |
| 4,678,184 | 7/1987 | Neiger et al. . | |
| 4,728,102 | 3/1988 | Pauls | 73/379 X |

Primary Examiner—Charles A. Ruehl
Attorney, Agent, or Firm—James J. Brown

[57] ABSTRACT

A device for measuring linear force which is converted to rotational force or torque. Initially, force is applied in a linear direction to a means for transmitting that force to a rotatable shaft where it is converted to rotational force which can be measured by a strain gauge. The device is mounted on a vertically adjustable column attached to a moveable base.

14 Claims, 5 Drawing Sheets

ISOMETRIC LIFTING DEVICE

SUMMARY OF THE INVENTION

The present invention is directed to a device for use in rehabilitative testing and therapy as well as physical conditioning generally which permits force applied by a person to the device from any of several directions to be measured isometrically. More specifically, the present invention is concerned with a structure which includes a moveable adjustable platform for the application of linear force and its transmittal and conversion into rotational force which can be measured and recorded isometrically on a torque measuring device.

BACKGROUND OF THE INVENTION

In the field of rehabilitative therapy as well as physical conditioning and training generally, various devices are known and used for isometrically measuring force applied by an individual. Such devices have, however, frequently had the disadvantage that they are limited to very specific forms and amounts of applied force and are not always suitable for use in measuring force which is applied using all of the various parts and functions of the human body. Typically, for example, such devices have involved merely attaching strain gauges directly to handles or other devices for transmitting limited amounts of exerted effort. Other devices have been constructed in such a way that they are unsuitable for measuring large forces since a portion of the force is applied to the structure of the device, rather than directly to the measuring instrument. Such a diversion of applied force not only produces an inaccurate recording of the force, but also can result in damage to the structure of the instrument.

It is according, an object of the present invention to provide a device for the isometric measurement of applied force by a system which directly transmits applied linear effort into rotational force which is then measured by a rotational torque measuring device. It is a further object of the present invention to provide a system for the isometric measurement of applied force in which the applied force is directly transmitted to the measuring device without the application of stress or strain to the structure supporting the measuring unit. Yet a further object of the present invention is to provide a system which is moveable and flexible and which permits the application of linear motion and force from different directions and in different ways in order to accommodate the various functions which typify human work effort.

DETAILED DESCRIPTION OF THE INVENTION AND A PREFERRED EMBODIMENT THEREOF

In accordance with the present invention, a device is provided for measuring applied forces such as lifting, pulling or pushing, which comprises a platform having a base and an upright standard to support a system to which linear force is applied in various directions and transmitted to a rotational torque measuring device. The system of the present invention is vertically adjustable on the standard to accommodate both the type of exercise and the individual performing the exercise. Linear force is applied to the system through an adjustable handle and can be transmitted by means of a flexible connector to a shaft where the linear force applied to the flexible connector is converted to rotational force. Alternatively, linear force can be transmitted from the handle and converted to rotational force by means of a gear rack which engages a pinion gear on the shaft. Detachably connected to the shaft is a rotary torque measuring device which can contain a strain gauge to measure the rotational force exerted on the shaft. Since a counter rotational force or resistance is applied to the shaft by the torque measuring device which essentially equals the positive force being applied by the individual, the device is essentially isometric in the sense that there is virtually no actual movement of the connector or shaft in reaction to the applied force. The invention will however, be more fully appreciated by having reference to the drawings which are illustrative of a preferred embodiment thereof.

Figure 1:
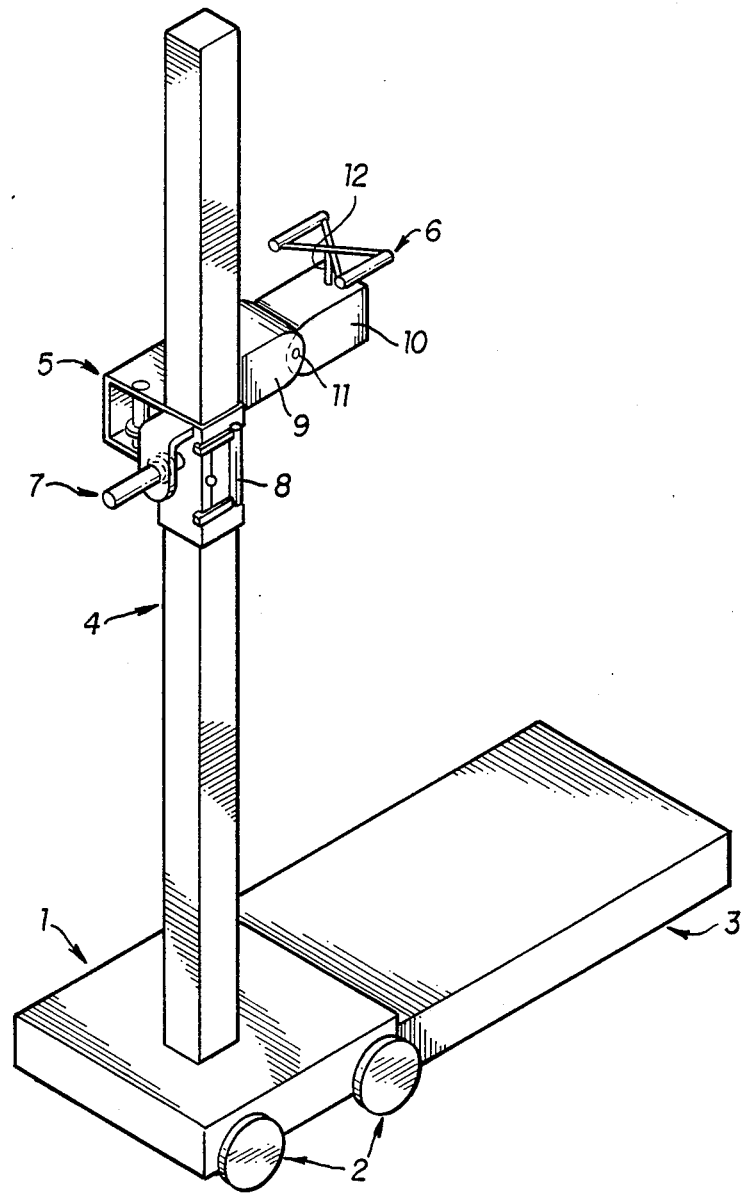
FIG. 1 is a perspective view of the device of the present invention adapted for engagement with a torque measuring instrument.

Directing attention to the drawings which are illustrative of a preferred embodiment of the invention, a generally flat, horizontal base 1 is shown having two pairs of wheels 2 to permit the device to be easily moved about. Mounted generally in the center of the base 1 is an upright standard 4 which can, for example, extend to a height of six feet or more. Slideably mounted on the standard 4 is the force transmission housing 5, which can be moved up and down as desired and locked onto the upright standard by means of a latch 8. The actual transmission housing 5 consists of two sections 9 and 10 which are joined by a pin 11 to permit section 10 to be moved in a 180 degree arc, so that the orientation of the work handle 6 can be changed as desired. Work handle 6 is attached to a flexible connector, such as a cable 12 which passes through the housing 5 and ultimately attaches to a rotatable shaft 7. Thus, any work effort applied by means of handle 6 to connector 12 is transmitted to the rotatable shaft 7 to cause a rotational force thereon. Although not shown in FIG. 1, the shaft 7 can attach to a rotary torque measuring device such as described in U.S. Pat. No. 4,475,408 to Browning, and shown in FIG. 6 of the drawings. This device provides a contra-rotational force or resistance which opposes the rotational force applied by the user of the device to the shaft 7 and registers the amount of applied force. Usually, the rotary torque measuring device itself will be mounted independently in its own supporting structure to permit coupling of the shaft 7 to the torque measuring device. Alternatively, a strain gauge can be immovably mounted so that it does not turn and coupled directly to the shaft. An extension 3 of the base 1 is conveniently provided for the individual using the device to stand on.

Figure 4:
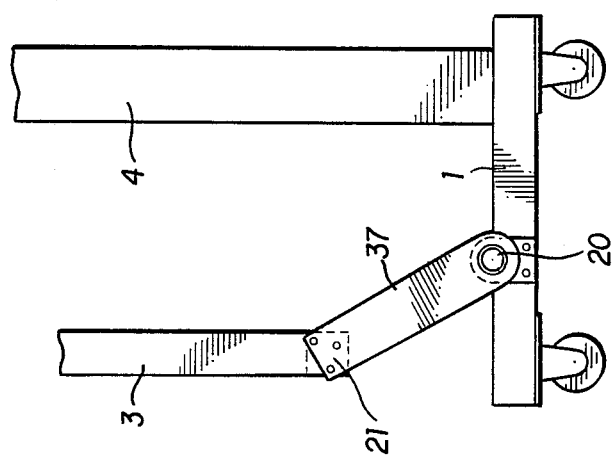
FIG. 4 is a side view illustrating the folded-up configuration of the base of the invention.
Figure 3:
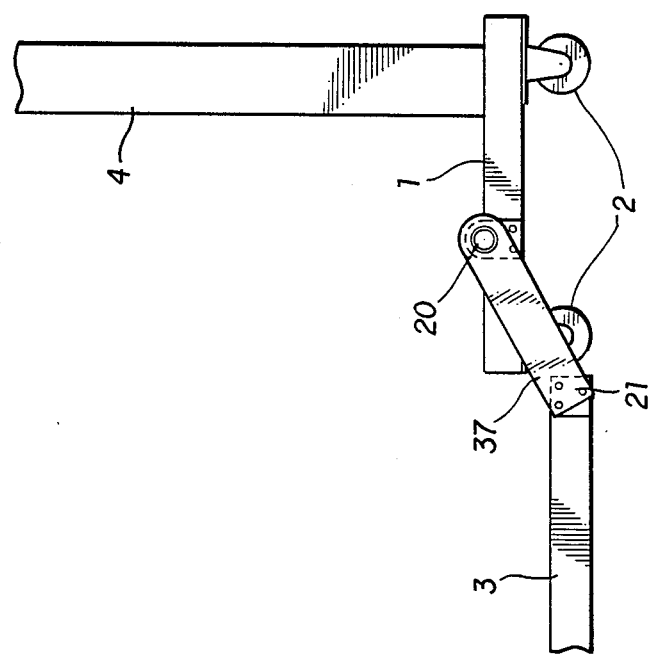
FIG. 3 is a side view illustrating the fold-up base of the invention in one position.

This base is attached by means of an extension 37 and hinges 20 and 21 to the base 1 so that it can be folded into an upright position when not in use. The respective configurations of the folding base 3 are illustrated in FIGS. 3 and 4 of the drawings.

Figure 2:
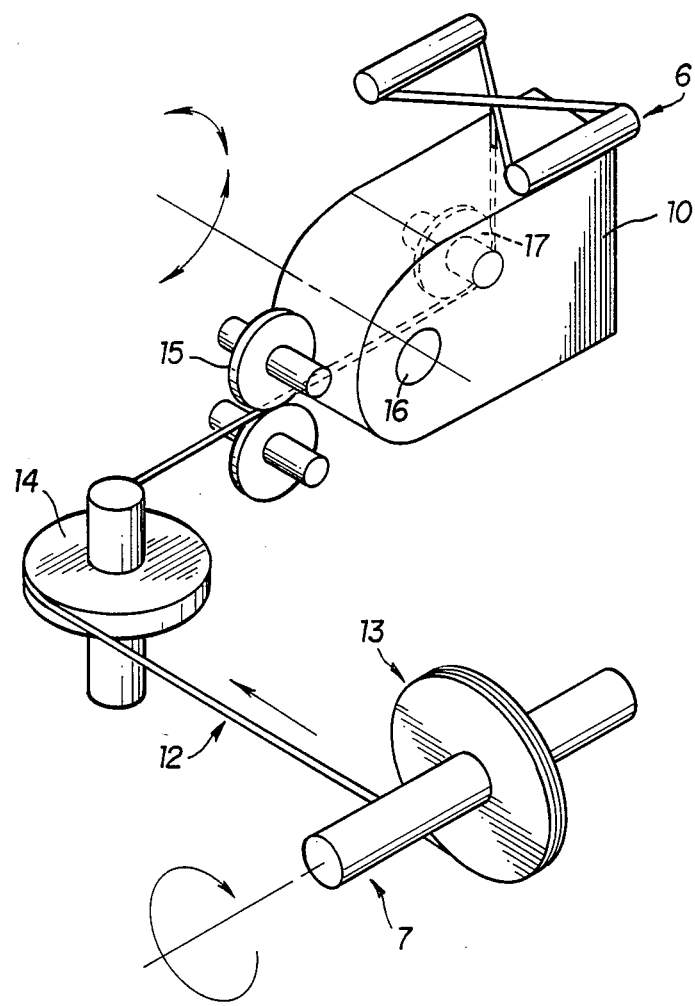
FIG. 2 is a detailed break-away schematic drawing illustrating the structure of the force transmission components of the invention.

The details of the structure of the force transmission housing 5 will be more fully appreciated by having reference to FIG. 2 of the drawings. Directing attention to this figure, the handle 6 attaches to flexible connector 12 which typically can be a steel cable. The flexible connector 12 ultimately attaches to pulley 13 which is mounted on horizontal shaft 7 so that any pulling force exerted by means of handle 6 on the flexible connector 12 in the linear direction of the arrow shown is exerted on the pulley 13 and imparts a rotational torque or force on the shaft 7. The direction of the extension of the flexible connector 12 is changed by approximately 90 degrees by having it engage and bend around pulley 14 mounted on a vertically disposed shaft. The flexible connector after passing across the pulley 14 is channeled between the two rotating wheels 15 into the adjustable assembly housing 10 where it engages pulley 17 and is diverted upward at approximately 90 degrees to engage the handle 6. Assembly housing 10 is provided with a hole 16 to accommodate the pin 11 shown in FIG. 1 and permit the housing 10 to be adjusted so that the handle can assume various orientations depending upon the direction of force to be applied thereto. Irrespective, however, of the orientation of the handle 6, any linear force which is applied to the flexible connector 12 through the handle will be transmitted to shaft 7 and ultimately converted directly into rotational torque. Shaft 7 is itself coupled to a rotary torque measuring device which is not shown in the drawing. Because of the system of pulleys and the use of the flexible cable, all nonrotational force applied to the handle 6 is taken by the column 4, while only the rotational component of the force (the torque) is directed to the shaft 7 which avoids placing stress on the supporting structure and allows an accurate measurement of the force being exerted on the system.

Figure 5:
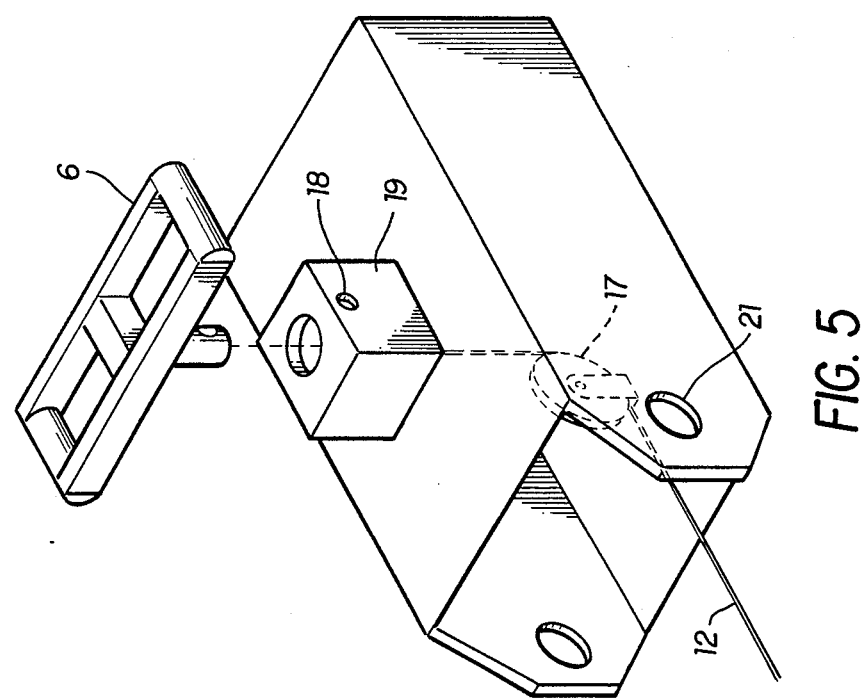
FIG. 5 is a detailed schematic illustration of the connection between the handle and flexible connector of the invention.

FIG. 5 illustrates the manner in which handle 6 is attached to the flexible connector 12. A cradle block 19 is attached to the flexible connector 12. The end of the flexible connector 12 is a threaded stud which threads into the base of the cradle 19. The cradle 19 has a hole at the top into which the handle 6 can be inserted. There are transverse holes 1B in the handle 6 shaft and cradle 19, into which a quick pin can be inserted to lock the handle to the cradle 19 and hence to the flexible connector 12.

Figure 6:
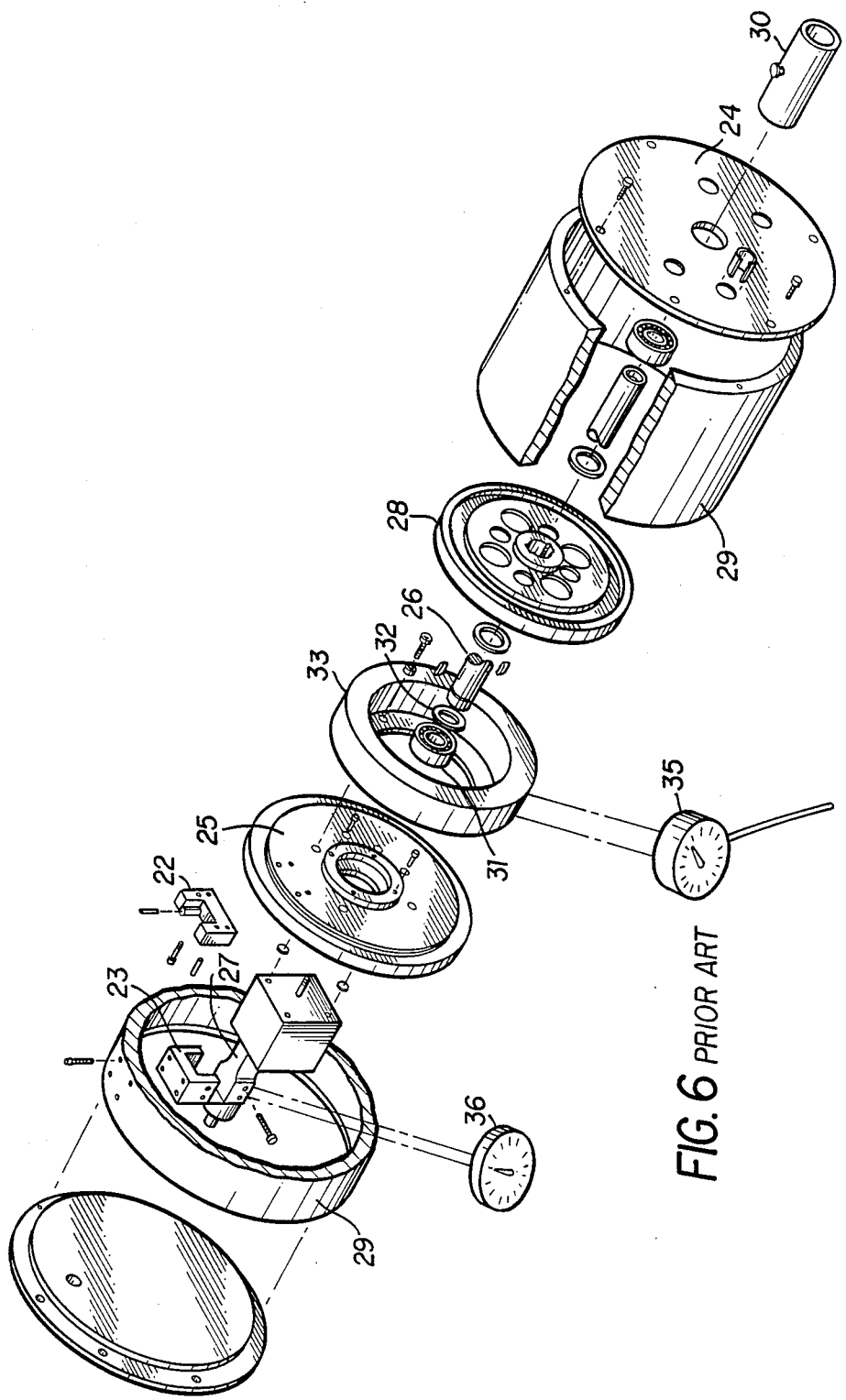
FIG. 6 illustrates in detail a torque measuring instrument for use in the invention.

The torque measuring device which can be employed in accordance with this invention is shown in FIG. 6 of the drawings and permits the measurement of rotational force applied to the shaft. A rotatable magnetizable disc 28 is mounted on the rotatable shaft 26 adjacent an electric friction brake 33 which is adapted to engage and restrain rotation of the disc and the shaft when an electric current is applied to the brake to produce a magnetic force. The brake is disposed so as to allow the shaft to rotate freely in the absence of an electric current.

The brake and its associated mounting plate 25 are mounted perpendicular to and concentric with the axis of the rotatable shaft 26 and mounted in a manner which allows them to rotate freely as a unit about the shaft axis.

A strain gauge 27 is mounted such that one end is stationary and immoveable, the other end is mounted off axis to the brake mounting plate 25 such that the gauge prevents rotation of the brake mounting plate. Thus when a rotational force is applied to the brake mounting, the plate is restrained from moving by transmitting the force to the strain gauge thus stressing the gauge and causing an electrical signal to be present at the output of the strain gauge proportional to the stress inflicted on the gauge which is in turn proportional to the rotational force.

It will be understood that the description of an electric gauge is exemplary and that other devices for measuring torque or rotational force applied to the shaft, which can be mechanical, hydraulic or electrical can be used as well.

A coupling is provided at 30 to accommodate the shaft 7 and permit transmittal of rotational force from the shaft to the measuring device. The shaft assembly 26 is mounted such that one end of the shaft is inserted in the central bearing of the brake mounting plate and the other end inserted in the bearing central to the front cover 24. The snap rings occurring inside of their respective bearings prevent axial movement of the shaft. This positions the armature in close proximity to the brake magnet with its smooth face parallel to that of the magnet and its axis of rotation coincident with that of the brake mounting plate.

It can be seen that when a turning force is exerted on the shaft, the shaft and the armature are free to rotate within the assembly. An electric current is passed from voltage control 35 through the brake magnet and a magnetic force is produced at its face proportional to the magnitude of current flow. This magnetic force attracts the armature which is allowed to move axially along the shaft until the face of the armature contacts the face of the brake magnet. The face of the brake magnet is friction material. It can be seen that while current is flowing in the brake, the armature is attracted into intimate contact with the friction material and is retarded from rotating. The amount of retardation is a function firstly of the coefficient of friction between the friction material and the armature material, secondly of the force normal, and thirdly of the radius of gyration. The force normal being variable owing to its relationship to the magnitude of current flow.

Relative motion between the magnet and the armature is possible while current is flowing only if sufficient rotational force is applied to the shaft to overcome the retarding effect of the brake magnet. In order for motion to continue, the rotational force must be maintained on the shaft. In this system, the only thing preventing the brake assembly from rotation while current is flowing is the strain gauge. In this manner, any rotational force applied to the shaft while current is flowing is felt by the strain gauge and an output from the gauge is seen which is directly proportional to the force exerted on the shaft.

Of course, if an immovably mounted strain gauge is coupled directly to the shaft, the entire brake mechanism is no longer needed since no rotation of the shaft is possible.

As already noted, the handle, and force transmission housing, are mounted together on vertical standard 4, so that the unit can be vertically adjusted to accommodate various individual and types of work effort. Adjustment of the angle of the handle 6 also permits the application of different types of effort such as pulling, lifting or pushing. The torque measuring device will usually be mounted independently, but in such a way that the shaft 7 engages the coupler 30.

What is claimed is:

1. A device for measuring applied force which comprises a rotational shaft attached to means for registering rotational force applied thereto; an elongated connector means attached to said shaft for transmitting force exerted in a linear direction, said connector means attached to said shaft extending away from said shaft at an angle to the longitudinal axis thereof, said elongated connector means terminating in handle means for applying said linear force to said connector means in a direction away from said means and along the extended longitudinal axis thereof such that said applied linear force is transmitted directly to said rotatable shaft and converted to said rotational force; said handle means being attached to said connector means by means for varying the angle through which said force is applied to said connector means.

2. The device of claim 1 wherein said connector means extend linearly away from said shaft and engage consecutively one or more means for altering the direction of said linear extension.

3. The device of claim 2 wherein said means for altering the direction of said connector means are pulleys or bearings.

4. The device of claim 2 wherein said connector means is a rope or cable.

5. The device of claim 1 wherein said means for registering rotational force includes a brake means for controllably opposing said applied force and a strain gauge for measuring said force.

6. The device of claim 1 which is mounted on a vertically extensible platform such that the vertical height of said means for applying force to said connector means can be varied.

7. The device of claim 6 wherein said platform is provided with a base.

8. A device for measuring applied linear force which comprises in combination a platform having a base which engages an upright standard which supports in a vertically adjustable position, means for transmitting applied rotational force to a rotatable shaft comprising a flexible elongated connector means for transmitting said applied linear force to said rotational shaft attached at one end thereof, said elongated connector means extending linearly away from said shaft at right angles to the longitudinal axis thereof, said elongated connector means terminating in handle means for applying said linear force to said connector means in a direction away from said connector means and along the extended longitudinal axis thereof such that said applied linear force is transmitted to said rotatable shaft and converted to said rotational force; said handle means being attached to said connector means by means for varying the angle through which said force is applied to said connector means.

9. A device for measuring applied linear force which comprises in combination a platform having a base which engages and upright standard which supports in a vertically adjustable position: means for transmitting applied rotational force to a rotatable shaft comprising a flexible elongated connector means for transmitting said applied linear force to said shaft attached at one end thereof, said elongated connector means extending linearly away from said shaft to engage consecutively one or more means for altering the direction of said linear extension, said elongated connector means terminating in handle means for applying said linear force to said connector means along the extending longitudinal axis thereof such that said applied linear force is transmitted directly to said rotatable shaft and converted to said rotational force; means for registering applied rotational force coupled to said rotable shaft and including a brake for providing a controlled force to oppose said applied force and a strain gauge for registering said applied force; said handle means being attached to said connector means by means for varying the angle through which said force is applied to said connector means.

10. A device for measuring applied linear force which comprises in combination a platform having a moveable base including a foldable horizontal extension thereof, said base engaging an upright standard which supports in a vertically adjustable position; means for transmitting applied rotational force to a rotatable shaft, a flexible elongated connector means for transmitting said applied linear force to said shaft attached at one end thereof, said elongated connector means extending linearly away from said shaft to engage consecutively one or more means for altering the direction of said linear extension, said elongated connector means terminating in means for applying said linear force to said connector means along the extended longitudinal axis thereof such that said applied linear force is transmitted to said rotatable shaft and converted to said rotational force; means for registering applied rotational force including an electromagnetically actuated friction brake means for providing a controlled force to oppose said applied rotational force and a strain gauge for registering said applied force.

11. The device of claim 10 wherein said platform is provided with a base.

12. A force registering device which comprises a rotational shaft adapted to be attached to measn for registering rotational force applied thereto; connector means attached to said shaft for transmitting applied force exerted through a handle attached thereto in a linear direction, said connector means attached to said shaft such that said applied linear force is transmitted directly to said rotationable shaft and converted to said rotational force, said handle being attached to said connector means by means for varying the angle through which said linear force is applied to said connector means.

13. The device of claim 12 wherein said means for registering rotational force includes a brake means for controllably opposing said applied force and a strain gauge for measuring said force.

14. The device of claim 12 which is mounted on a vertically extensible platform such that the vertical height of said means for applying force to said connector means can be varied.

* * * * *